United States Patent [19]

Levy

[11] 3,965,166

[45] *June 22, 1976

[54] OXIDATION OF OLEFINS

[75] Inventor: Leon B. Levy, Corpus Christi, Tex.

[73] Assignee: Celanese Corporation, New York, N.Y.

[ * ] Notice: The portion of the term of this patent subsequent to June 22, 1993, has been disclaimed.

[22] Filed: Feb. 24, 1969

[21] Appl. No.: 801,766

[52] U.S. Cl. .................... 260/533 N; 260/530 N; 252/467
[51] Int. Cl.² ..................................... C07C 51/32
[58] Field of Search .................... 260/533 N, 530 N

[56] References Cited
UNITED STATES PATENTS

| | | | |
|---|---|---|---|
| 3,405,172 | 10/1968 | Brown et al. | 260/533 N |
| 3,435,069 | 3/1969 | Bethell et al. | 260/533 N X |
| 3,497,553 | 2/1970 | Trapano | 260/533 N |
| 3,776,952 | 12/1973 | Ogden | 260/533 N |

FOREIGN PATENTS OR APPLICATIONS

| | | | |
|---|---|---|---|
| 1,366,301 | 6/1964 | France | 260/533 N |
| 1,554,240 | 1/1969 | France | 260/533 N |
| 41-14982 | 8/1966 | Japan | 260/530 N |

*Primary Examiner*—Anton H. Sutto
*Attorney, Agent, or Firm*—Stewart N. Rice; Ralph M. Pritchett

[57] ABSTRACT

Process for the oxidation of olefins to the corresponding unsaturated aldehydes and acids, e.g. propylene to acrolein and acrylic acid, by reacting the olefin with oxygen in the presence of a catalyst of the empirical formula $Mo_xCr_yTe_zO_n$. When $x$ is 100, $y$ is 10–50, $z$ is 0.1–10, and $n$ is 300–500.

9 Claims, No Drawings

OXIDATION OF OLEFINS

BACKGROUND OF THE INVENTION

The present invention relates to a process for the oxidation of olefins to produce unsaturated aldehydes or mixtures of unsaturated aldehydes with unsaturated acids and to a novel catalyst therefor.

The production of unsaturated aldehydes and unsaturated carboxylic acids, e.g. acrolein and acrylic acid, has become of significant commercial interest in recent years and therefore many processes have been developed for the production of these products. One of such processes is by converting olefins to a higher oxidation state by reacting an olefin with oxygen in the presence of a catalyst. For example U.S. Pat. No. 3,392,196 describes such a process wherein a catalyst of the empirical formula $Mo_{10}Mn_2P_{2-20}O_{39-120}$ is utilized for the oxidation of propylene or isobutylene to form acrolein, methacrolein and acrylic acid or methacrylic acid. Many other catalysts are also known for such oxidations; however, research is constantly underway for new and improved processes and catalysts since most catalysts presently known suffer such disadvantages as short catalyst life, low conversions and/or low selectivities to desired products.

SUMMARY

It is thus an object of the present invention to provide a process for the preparation of products of a higher oxidation state from olefinic hydrocarbons. A further object of the present invention is to provide a process by which acrolein and acrylic acid may be prepared from propylene. Another object of the present invention is to provide a novel catalyst suitable for the oxidation of olefins to unsaturated aldehydes and unsaturated acids at high conversions and high selectivities. Additional objects will become apparent from the following description of the present invention.

These and other objects are accomplished by the present invention which in one of its embodiments is a process by which an ethylenically unsaturated hydrocarbon may be oxidized to the corresponding ethylenically unsaturated aldehyde or mixtures thereof with the corresponding ethylenically unsaturated carboxylic acid, said process comprising reacting in the gas phase said ethylenically unsaturated hydrocarbon with oxygen in the presence of a catalyst of the empirical formula: $Mo_xCr_yTe_zO_n$ wherein $x$, $y$, $z$, and $n$ are numbers such that the atomic ratio of Mo:Cr:Te:O is 100:10–50:0.1–10:300–500. In another embodiment the present invention is said catalyst of the formula $Mo_xCr_yTe_zO_n$.

DESCRIPTION OF THE PREFERRED EMBODIMENT

The novelty of the present invention resides mainly in the novel catalyst of the formula $Mo_xCr_yTe_zO_n$ and, as was pointed out above, generally $x$, $y$, $z$, and $n$ are numbers such that the atomic ratio of Mo:Cr:Te:O is 100:10–50:0.1–10:300–500. However, it is preferred that this ratio be 100:10–40:0.2–5.0:330–460. The number of atoms of oxygen or the number assigned to $n$ is determined by the valence requirements of the molybdenum, chromium, and tellurium and is usually approximately equal to $3x$ plus $3y$ plus $2z$. The ratio of the various metals to each other, particularly the amount of tellurium is fairly critical and should be maintained with the broad limits expressed above. As may be seen from the above, the amount of tellurium in the catalyst will generally be below about 10 weight percent based on the combined weight of molybdenum and tungsten present.

The catalysts of the present invention may be considered as a mixture of the oxides of the various metals and/or as true compounds of a coordinate complex structure, e.g. a heteropoly compound such as a telluromolybdochromate or a mixture of chromium molybdate and tellurium dioxide. The catalyst may be formed by various methods but the most preferred method for forming the catalyst when it is to be used in the oxidation of olefins is to calcine a solid obtained by combining (a) a molybdic acid or ammonium salt thereof, (b) ammonium chromate or a water-soluble chromium salt of an organic or inorganic acid, and (c) an inorganic tellurium compound, preferably telluric acid, ammonium tellurate or a tellurium oxide. An ammonium molybdate is the preferred source of molybdenum while the preferred source of chromium is ammonium chromate, chromic nitrate or a water-soluble chromium salt of a $C_1$ to $C_8$ carboxylic acid. Calcining as used herein involves heating at temperatures on the order of 200° to 600°C in the presence of air or other molecular oxygen-containing gases. Several methods can be utilized for forming the mixtures of the metal compounds which are to be calcined. For example an aqueous solution of the molybdenum and chromium compounds may be mixed with the tellurium compound (in the form of a water-soluble compound, a water-insoluble compound or as a solution in an aqueous solvent such as water itself or hydrochloric acid) followed by evaporation of the liquid to obtain a cake which is dried and calcined. The catalyst is preferably granulated or pelleted before use and this may be accomplished either before or after calcining.

A specific method of forming a catalyst involves blending water-insoluble tellurium dioxide with an aqueous solution of ammonium paramolybdate and either chromic acetate or ammonium chromate, followed by evaporating the water from the resulting suspension to obtain a cake which is dried and calcined. An aqueous solution of ammonium chromate may be obtained by dissolving chromic acid in ammonium hydroxide. Another method includes the steps of forming a solution of ammonium paramolybdate and chromic acetate, evaporating the solution to obtain a cake, thoroughly mixing the cake with tellurium dioxide in the presence of water (although not necessarily enough water to completely dissolve the cake) followed by evaporation of the water and calcining. Alternatively an aqueous solution of ammonium paramolybdate and chromic acetate may be mixed with a solution of tellurium dioxide in aqueous hydrochloric acid followed by evaporation of the liquid and calcining the resulting cake. In this latter method an aqueous solution of ammonium tellurate or telluric acid could be substituted for the solution of tellurium dioxide in hydrochloric acid.

Some specific compounds useful in forming the catalysts according to the above procedure are ammonium paramolybdate, chromic acetate, chromic nitrate, ammonium chromate, tellurium dioxide, tellurium trioxide, and telluric acid.

The catalysts of the present invention may be employed as such or may be used in connection with a suitable catalyst support although it is preferred that the catalyst be utilized without a support. When a support is present as part of the catalyst composition, the support will usually comprise from about 20 to 99% by weight, preferably 80 to 98% by weight, of the catalyst composition.

The oxidation process of the present invention may be carried out continuously or non-continuously and the catalyst may be present in various forms such as in fixed beds or as a fluidized system. Portions of the reactants which do not undergo reaction may be recycled if desired. Also where it is desired to produce an unsaturated acid as the ultimate product it may be desirable to recycle at least a portion of the unsaturated aldehyde formed during the reaction.

The temperatures utilized in conducting the oxidation should generally be between about 250° to 550°C although the exact temperature utilized in a particular situation will depend largely on the desired product composition. Thus if it is desired to produce an oxygenated product consisting largely of unsaturated aldehydes with no or at least small amounts of unsaturated acids present, then temperatures in the range of 250° to 400°C are preferred. However if it is desired to produce a product which contains minor portions of unsaturated acid in addition to the major portions of unsaturated aldehyde, then higher temperatures in the range of 350° to 550°C are preferably utilized. The production of mixtures of unsaturated aldehydes and acids are generally most advantageous when the product is to be further oxidized in a second step so as to produce unsaturated acids as the ultimate end product. For example a two step process may be utilized for converting propylene to acrylic acid.

The pressure utilized in the process of the present invention may be subatmospheric, atmospheric or superatmospheric and should be between about 0.5 and 3.0 atmospheres for best results, although pressures ranging up to 7.0 atmospheres and higher may be suitably employed. The contact time of the reactants with the catalyst at the reaction conditions should generally be between about 0.1 and 15 seconds but is preferably a time within the range of 0.5 to 10 seconds. As used herein the term contact time refers to the contact time adjusted to 25°C and atmospheric pressure (conditions denoted by NTP). Thus the contact time is calculated by dividing the volume of the catalyst bed (including voids) by the volume per unit time flow rate of the reactants at NTP.

The oxygen necessary as a reactant in the present process may be from concentrated molecular oxygen or may be from a more dilute oxygen-containing gas wherein the molecular oxygen is mixed in varying amounts with an inert diluent gas such as nitrogen, argon, or carbon oxides. For instance air may be utilized as the source of oxygen. The ethylenically unsaturated hydrocarbon and/or oxygen-containing gas may be separately introduced into the reaction zone at one or a plurality of points along the length of the reaction zone or may be premixed before entering the reaction zone. However the contact of the olefin and the oxygen-containing charge are preferably kept to a minimum before entering the reaction zone. The reactants may be pretreated before entering the reaction zone such as for the removal of undesirable components therefrom.

In conducting the oxidation reaction, the gaseous feed mixture should generally contain from about 0.5 to 7.0 moles of oxygen per mole of the ethylenically unsaturated hydrocarbon although the preferable range is from 1.0 to 5.5 moles per mole. Although it is not required, water is also desirably present in the gaseous feed in amounts of from 1.5 to 15, preferably 5.0 to 12 moles per mole of unsaturated hydrocarbon. Care should be taken to avoid contacting the catalyst with liquid water during operation. In addition to water, diluents which are gaseous under the reaction conditions and are relatively inert may be introduced into the system. Suitable diluents include $CO_2$, nitrogen and flue gas as well as paraffinic hydrocarbons such as are frequently present in commercially-available propylene and isobutylene, for example mixtures of propane and propylene obtained from cracking units.

The ethylenically unsaturated hydrocarbons that may be oxidized in accordance with the present invention are preferably $\alpha$-olefins of 3 to 5 carbon atoms. The present process is best suited for the conversion of propylene and isobutylene.

The following examples are given in order to illustrate but not to limit the scope of the present invention. In the examples selectivity and conversion are defined as follows:

$$\text{Conversion, \%} = \frac{\text{moles olefin converted}}{\text{moles olefin fed}} \times 100$$

$$\text{Selectivity, mole \%} = \frac{\text{moles of desired product}}{\text{moles olefin converted}} \times 100$$

EXAMPLE I

Solutions of ammonium molybdate tetrahydrate (30.0 g in 50 ml of water), chromic acetate monohydrate (12.0 g in 50 ml of water) and tellurium dioxide (0.141 g in 10 ml of concentrated hydrochloric acid) were mixed and then the mixture was evaporated to dryness at 110°C. The solid obtained was then calcined at 400°C for 16 hours and screened to −10 +16 mesh U.S. The catalyst obtained may be represented by the formula $Mo_{100}Cr_{28.6}Te_{0.52}O_{387}$.

EXAMPLE II

Several runs were made for the oxidation of propylene to acrolein and acrylic acid utilizing the catalyst of Example I as well as a catalyst of the formula $Mo_{100}Cr_{28.6}Te_{2.1}O_{390}$. This latter catalyst was prepared in the same manner as that of Example I except that the amount of $TeO_2$ utilized in the preparation was increased to 0.564 g. In all of the runs the contact time was 2.0 seconds (NTP) and the feed mixture of propylene, air and water was such that the molar ratio of oxygen to propylene was about 3.4:1 and the molar ratio of water to propylene about 7.7:1. The results of the several runs are shown in the following table.

| Run | Catalyst | Temp. °C | Conversion, % | Selectivity, mol % Acrolein | Acrylic Acid |
|---|---|---|---|---|---|
| 1 | $Mo_{100}Cr_{28.6}Te_{0.52}O_{387}$ | 324 | 31 | 70 | 2 |
| 2 | " | 350 | 80 | 47 | 9 |

-continued

| Run | Catalyst | Temp, °C | Conversion, % | Selectivity, mol % Acrolein | Selectivity, mol % Acrylic Acid |
|---|---|---|---|---|---|
| 3 | " | 400 | 99 | 13 | 5 |
| 4 | $Mo_{100}Cr_{28.6}Te_{2.1}O_{390}$ | 327 | 57 | 86 | 3 |
| 5 | " | 350 | 88 | 61 | 15 |

The embodiments of the invention in which an exclusive property or privilege is claimed are defined as follows:

1. A process by which an alpha olefin having from 3 to 5 carbon atoms may be oxidized to the corresponding ethylenically unsaturated aldehyde or mixtures thereof with the corresponding ethylenically unsaturated carboxylic acid, said process comprising reacting in the gas phase said olefin with oxygen in the presence of a catalyst consisting essentially of the empirical formula:

$$Mo_xCr_yTe_zO_n$$

wherein $x$, $y$, $z$ and $n$ are numbers such that the atomic ratio of Mo:Cr:Te:O is 100:10–50:0.1–10:300–500; at a temperature sufficient to produce the desired product.

2. The process of claim 1 wherein propylene is oxidized to produce acrolein or mixtures of acrolein and acrylic acid or wherein isobutylene is oxidized to methacrolein or mixtures of methacrolein and methacrylic acid.

3. The process of claim 2 wherein the temperature is from about 250°–550°C, the pressure is from about 0.5 to 7.0 atmospheres, wherein water is present in amounts of from about 1.5 to 15 moles per mole of said hydrocarbon, and wherein oxygen is present in amounts of from about 0.5 to 7.0 moles per mole of said hydrocarbon.

4. The process of claim 3 wherein said catalyst is unsupported.

5. The process of claim 3 wherein $x$, $y$, $z$, and $n$ are numbers such that the atomic ratio of Mo:Cr:Te:O is 100:15–40:0.2–5.0:330–460 and wherein the contact time (NTP) of the reactants with the catalyst is from about 0.5 to 10 seconds.

6. The process of claim 5 wherein said catalyst is unsupported.

7. The process of claim 3 wherein said catalyst is one having been obtained by calcining a solid obtained by combining (a) a molybdic acid or an ammonium molybdate, (b) either ammonium chromate or a water-soluble chromium salt of an inorganic or organic acid, and (c) an inorganic tellurium compound.

8. The process of claim 7 wherein said inorganic tellurium compound is telluric acid, ammonium tellurate or a tellurium oxide and wherein said water-soluble chromium salt is chromic nitrate or a salt of a $C_1$ to $C_8$ carboxylic acid.

9. The process of claim 8 wherein said catalyst is unsupported and wherein the atomic ratio of Mo:Cr:Te:O is 100:15–40:0.2–5.0:330–460.

* * * * *